US009612194B2

(12) United States Patent
Davis et al.

(10) Patent No.: US 9,612,194 B2
(45) Date of Patent: Apr. 4, 2017

(54) SPECTROSCOPIC ANALYSIS OF OIL SANDS ORE FACE FOR REAL TIME ORE BLEND MANAGEMENT

(75) Inventors: Michael A. Davis, Glastonbury, CT (US); Andrew E. Carlson, Higganum, CT (US); David O. Winkowski, Wethersfield, CT (US); John V. Viega, Ellington, CT (US); Alan D. Kersey, South Glastonbury, CT (US); Mark R. Fernald, Enfield, CT (US)

(73) Assignee: CiDRA Corporate Services Inc., Wallingford, CT (US)

( * ) Notice: Subject to any disclaimer, the term of this patent is extended or adjusted under 35 U.S.C. 154(b) by 349 days.

(21) Appl. No.: 14/131,035

(22) PCT Filed: Jul. 9, 2012

(86) PCT No.: PCT/US2012/045942
§ 371 (c)(1),
(2), (4) Date: Apr. 24, 2014

(87) PCT Pub. No.: WO2013/006853
PCT Pub. Date: Jan. 10, 2013

(65) Prior Publication Data
US 2014/0347472 A1    Nov. 27, 2014

Related U.S. Application Data

(60) Provisional application No. 61/505,355, filed on Jul. 7, 2011.

(51) Int. Cl.
| | |
|---|---|
| *G01N 21/27* | (2006.01) |
| *H04N 5/33* | (2006.01) |
| *G01N 21/31* | (2006.01) |
| *G01N 33/24* | (2006.01) |
| *G01N 21/3563* | (2014.01) |
| *G01G 19/08* | (2006.01) |

(Continued)

(52) U.S. Cl.
CPC ............. *G01N 21/27* (2013.01); *G01G 19/08* (2013.01); *G01N 21/31* (2013.01);
(Continued)

(58) Field of Classification Search
CPC ........ G01N 21/27; G01N 21/31; G01N 21/84; H04N 5/33; G06T 7/00; G01G 19/08
See application file for complete search history.

(56) References Cited

U.S. PATENT DOCUMENTS 4,337,396 A * 6/1982 Lauer ................. G01N 21/3563
250/255
4,355,231 A    10/1982 Lauer et al.
(Continued)

OTHER PUBLICATIONS

Boulanger et aL .. Virtualized Reality: An Application to Open-Pit Mine Monitoring, Dec. 2000 (Dec. 2000) [retrieved on Oct. 13, 2012 (Oct. 13, 2012)]. Retrieved from the Internet<URL: http://www.isprs.org/proceedingsIXXXIII/congress/part5/92_XXXIII-part5.pdf> entire document especially p. 94, para [0004]; Fig 4.

*Primary Examiner* — Dave Czekaj
*Assistant Examiner* — Nam Pham
(74) *Attorney, Agent, or Firm* — Ware, Fressola, Maguire & Barber LLP

(57) ABSTRACT

Apparatus is provided featuring a signal processor or signal processing module configured to receive signaling containing information about images of an ore sample; and determine information about a Bitumen Content of the ore sample based at least partly on the signaling, including for use in real time ore blend management in a bitumen recovery process related to mined oil sands. The ore sample may be an ore face, and the signaling may contain information about the images of the ore face. The signal processor or signal processing module may be configured to determine a real time ore face ore grade visualization based at least partly on the signaling, and provide corresponding signaling contain- (Continued)

ing information about the real time ore face ore grade visualization, including a composite overlay image.

59 Claims, 9 Drawing Sheets

(51) Int. Cl.
*G01N 21/84* (2006.01)
*G06T 7/00* (2017.01)

(52) U.S. Cl.
CPC ......... *G01N 21/3563* (2013.01); *G01N 21/84* (2013.01); *G01N 33/241* (2013.01); *G06T 7/00* (2013.01); *H04N 5/332* (2013.01); *G01N 2201/025* (2013.01); *G01N 2201/08* (2013.01); *G01N 2201/12* (2013.01); *G06T 2207/30181* (2013.01)

(56) References Cited

U.S. PATENT DOCUMENTS

| | | |
|---|---|---|
| 4,433,239 A | 2/1984 | Thompson |
| 4,474,616 A | 10/1984 | Smith et al. |
| 5,523,563 A | 6/1996 | Moessner |
| 5,781,336 A | 7/1998 | Coon et al. |
| 6,560,561 B1 | 5/2003 | Foster et al. |
| 6,782,970 B2 | 8/2004 | Chang |
| 6,872,946 B2 | 3/2005 | Tseng et al. |
| 7,067,811 B2 | 6/2006 | Long et al. |
| 7,162,463 B1 | 1/2007 | Wentland et al. |
| 7,339,169 B1 | 3/2008 | Eckels et al. |
| 2003/0015663 A1* | 1/2003 | Mikula ............ G01N 21/3563 250/339.11 |
| 2003/0173081 A1* | 9/2003 | Vinegar ............ E21B 43/243 166/272.1 |
| 2005/0000703 A1 | 1/2005 | Furuno et al. |
| 2005/0201592 A1 | 9/2005 | Peach et al. |
| 2006/0115201 A1 | 6/2006 | Heffels et al. |
| 2007/0222854 A1 | 9/2007 | Pochaopsky |
| 2009/0002187 A1 | 1/2009 | Kriel et al. |
| 2009/0147913 A1 | 6/2009 | Dragon et al. |
| 2009/0240481 A1 | 9/2009 | Durrant-Whyte et al. |
| 2010/0059667 A1* | 3/2010 | Ferguson ............ G01N 23/005 250/255 |
| 2011/0095186 A1* | 4/2011 | Falk ............ G01R 31/311 250/330 |
| 2012/0098654 A1* | 4/2012 | Ebert ............ E02F 9/24 340/438 |

* cited by examiner

Apparatus 10 a signal processor or signal processing module 12 configured to receive signaling containing information about images of an ore sample;

determine information about a Bitumen Content of the ore sample based at least partly on the signaling; including for use in real time ore blend management in a bitumen recovery process related to mined oil sands; and provide corresponding signaling containing the information about the Bitumen Content of the ore sample.

Figure 1a: The Basic Apparatus

---

The signal processor or signal processing module 12 a combination 14 of at least one processor and at least one memory including computer program code, where the at least one memory and the computer program code being configured, with the at least one processor, to cause the apparatus at least to determine the information about the Bitumen Content of the ore sample Figure 1b: The Signal Processor or Signal Processing Module 12

Figure 1

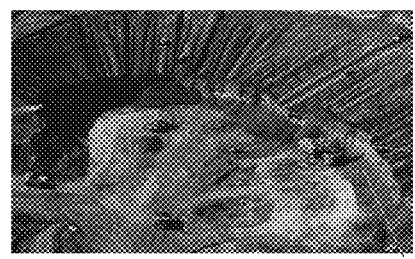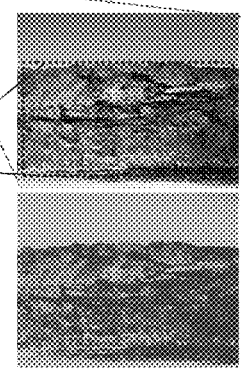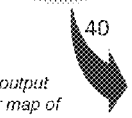
Figure 2a
Figure 2b
Figure 2c
Local 'worked' ore face visualization using a camera system capable of differential spectral image capture in visible & IR regions
Visualization system output provides a false color map of bitumen content in ore face
*Figure 2: Real Time Ore-Face Ore Grade Visualization for Smart Blend Management*

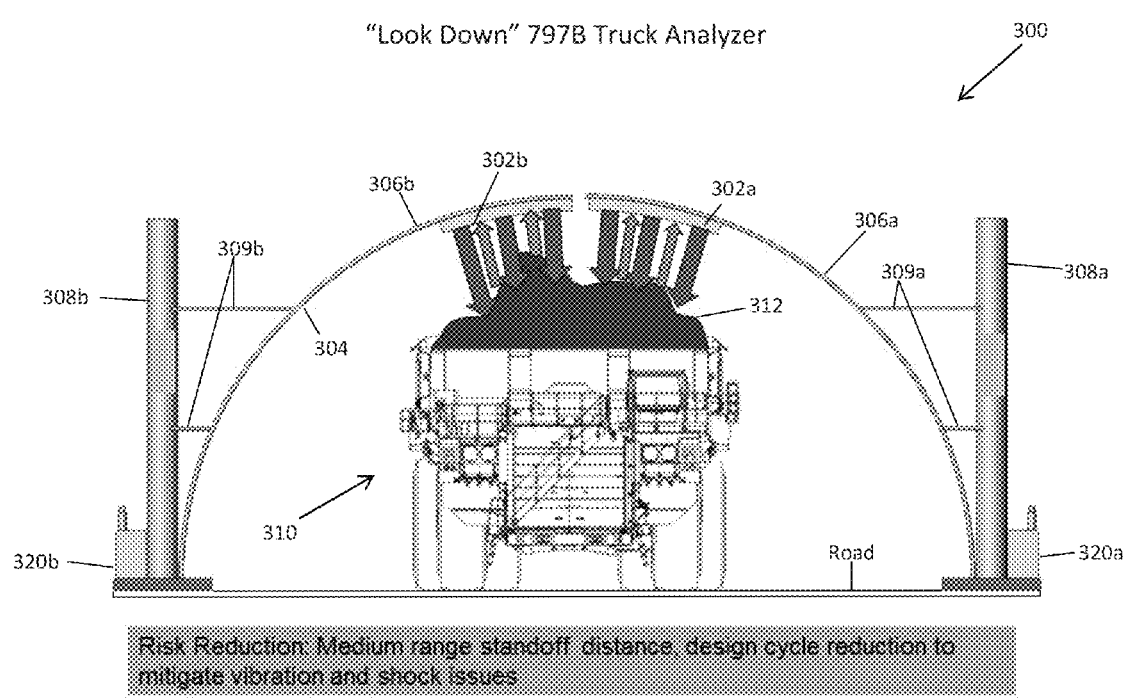
Figure 6: Drive-through device, structure or apparatus

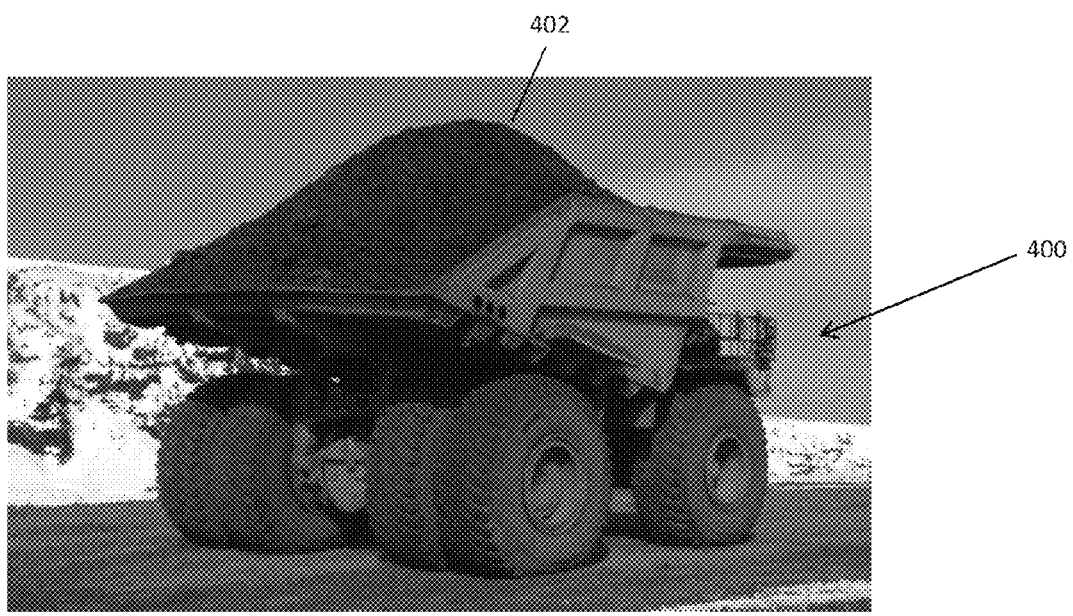
Figure 7: Truck with payload of bitumen ore

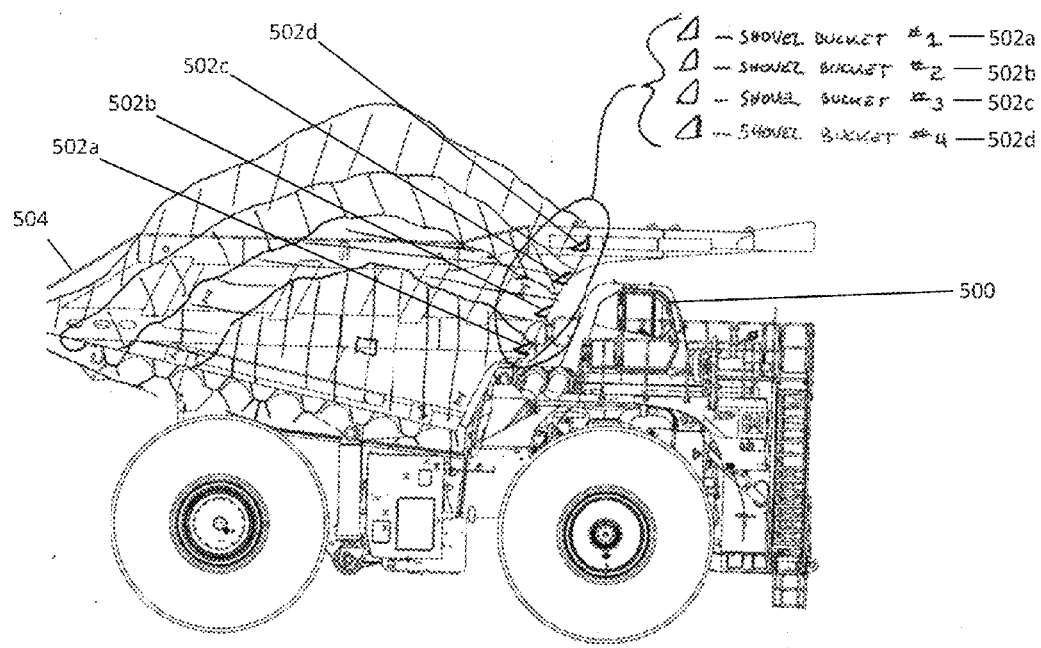
Figure 8: Truck having multiple devices to determine information about a bitumen content or an ore payload in the bed of the truck

SPECTROSCOPIC ANALYSIS OF OIL SANDS ORE FACE FOR REAL TIME ORE BLEND MANAGEMENT

CROSS-REFERENCE TO RELATED APPLICATIONS

This application corresponds to international paten application serial no. PCT/US2012/045942, filed 9 Jul. 2012, which claims benefit to provisional patent application Ser. No. 61/505,355 (CCS-0042), filed 7 Jul. 2011, which is incorporated by reference in their entirety.

BACKGROUND OF THE INVENTION

1. Field of Invention

The present invention relates to techniques for analyzing an ore sample; and more particularly relates to techniques for analyzing an ore sample to determine information about a Bitumen Content of the ore sample, including for use in real time ore blend management in a bitumen recovery process related to mined oil sands.

2. Description of Related Art

A key factor in the overall bitumen recovery performance in mined oils sands operations is the grade quality of the incoming mined ore. Bitumen recovery process plants are in general optimized for a particular in-coming ore grade, and variability in this grade can cause significant process variability, leading to non-optimum performance, losses in recovery and lower throughput, resulting in an impact to economic returns. Consequently, blend management techniques are utilized in an attempt to provide more consistent uniformity in the grade supplied to a recovery plant. Typically, this is accomplished by blending mined ore from multiple sections of the mine that are expected/projected to have different degrees of bitumen content. This model or mine map is based on the original (or subsequent follow on) core-sampling completed on the entire mine site to assess the geological and bitumen grade of the site. In this way, ore at say 12% bitumen content can be blended with ore at 10% content and ore at 8% content in a 3:2:1 ratio to produce a final blend at 10.7%.

Based on this approach a mine production plan can be developed which ensure relatively consistent ore grade input to the recovery plant through the life of the mine. While this has proven to be effective, the original mine map based on core samples does not provide very high-resolution mapping (core samples may be on a 100 m grid). The map is interpolated between these core samples to provide the resolution in the mapping. Consequently, mine-face shovel operators can experience significant variation in the ore quality being mined on a give day/shift compared to that projected by the mine map, as the interpolation between the core sample grid points cannot be relied on due to natural unforeseen geological variability.

SUMMARY OF THE INVENTION

According to some embodiments, the present invention may take the form of apparatus featuring a signal processor or signal processing module configured to receive signaling containing information about images of an ore sample; and determine information about a Bitumen Content of the ore sample based at least partly on the signaling, including for use in real time ore blend management in a bitumen recovery process related to mined oil sands.

According to some embodiments of the present invention, the apparatus may be used to provide a real time ore face ore grade visualization or a Total Bitumen Content (TBC) by percentage weight, consistent with that set forth herein.

According to some embodiments of the present invention, the apparatus may form part of, or be used to provide or implement, a drive-through device, structure or apparatus or a haul truck bed configuration, e.g., for analyzing a payload of ore in a bed of a haul truck at an ore pit, consistent with that set forth herein.

According to some embodiments of the present invention, the signal processor or signal processing module may comprise a combination of at least one processor and at least one memory including computer program code, where the at least one memory and the computer program code are configured, with the at least one processor, to cause the apparatus at least to receive the signaling and determine the information about the Bitumen Content of the ore sample. The signal processor or signal processing module may also be configured to provide corresponding signaling containing the information about the Bitumen Content of the ore sample, e.g., for use in real time ore blend management in a bitumen recovery process related to mined oil sands.

Real Time Ore Face Ore Grade Visualization

According to some embodiments of the present invention, the ore sample may be an ore face, and the signaling may contain information about the images of the ore face. The signal processor or signal processing module may also be configured to determine a real time ore face ore grade visualization based at least partly on the signaling, and provide corresponding signaling containing information about the real time ore face ore grade visualization, including a composite overlay image. In operation, an instrumented mining shovel may be configured to provide a shovel operator with real time imaging of the mine face, in effect for analyzing the ore face while retrieving the oil sands.

According to some embodiments of the present invention, the signaling may be received from a single or multiple cameras that image the ore face, including being adapted to, or forming part of, the instrumented mining shovel. The apparatus may comprise the single or multiple cameras. The images may be taken at various wavelength ranges and particular discrete wavelengths. The particular discrete wavelengths may include a wavelength at which bitumen strongly absorbs light, including visible, ultraviolet (UV) or infrared (IR), and a composite picture of the ore face is built. The composite picture may identify regions of bitumen-rich ore through a false color encoding of the image, including where strong absorption in reflected light, such as daylight or other illumination, is induced by the bitumen in surface layers, and the ore grade is indicated as most rich. The real time ore face ore grade visualization may provide for the ability, including by a mine-face operating shovel operator, to assess in real time, the grade quality of the ore being excavated, either providing confirmation that the ore is of an expected grade, or allowing a selective recovery/excavation to ensure an appropriate grade is mined at that location.

According to some embodiments of the present invention, the apparatus may form part of a Global Positioning Satellite (GPS) controlled system having hauling trucks that transport the ore to a process plant, each hauling truck configured with a respective signal processor, and the hauling trucks centrally dispatched to and from operating shovels in a mine or pit at a given time, where the GPS system allows for the ability, including by a mine operations team, to assess real-time the grade quality of any given truck load, and schedule payloads into the process plant in order to minimize substantially a blended ore grade variability. The apparatus may further comprise an optical arrangement configured to receive the images of the ore face and provide a composite overlay image containing information about the images of the ore face. The optical arrangement may comprise a single camera with a filter wheel; or a pair of camera tuned to different wavelength ranges, including a binocular differential waveband system having a visible camera and an infrared (IR) camera; or an integrated single detector array with pixels tuned to particular wavelengths of interest, including a camera with pixel filters. In each optical arrangement, a measurement of interest may rely on developing a contrast model/image from two images: one which is not dependent on the bitumen content (e.g., most likely to be the visible range or portion thereof), and one in which the bitumen absorbs strongly—e.g., near, short or mid infrared wavelengths. The signal processor or signal processing module may be configured to contrast the two images to each other, including being ratioed to produce a corresponding image highlighting the bitumen, e.g., including the bitumen content by percentage.

According to some embodiments of the present invention, the signal processor or signal processing module may comprise a combination of at least one processor and at least one memory including computer program code, where the at least one memory and the computer program code are configured, with the at least one processor, to cause the apparatus at least to receive the signaling and determine the real time ore face ore grade visualization, e.g., for use either by a mine-face shovel operator and/or a mine operations team in the real time ore blend management in a bitumen recovery process related to mined oil sands.

Total Bitumen Content by Percentage Weight

According to some embodiments of the present invention, the signal processor or signal processing module may be configured to determine a Total Bitumen Content (TBC) by percent weight through a spectroscopic technique that ratios several different absorption wavelengths of clay, water and bitumen.

According to some embodiments of the present invention, the signal processor or signal processing module may form part of a portable analyzer, an instrument or a geology tool, which is a hand held instrument that may be configured for real time field testing of ore content—to replace the necessity of taking samples to a lab for analysis.

According to some embodiments of the present invention, the apparatus may include a broadband spectral light source configured to illuminate the ore sample; a spectrometer configured to measure scattered light from the ore sample, including via an input fiber optic bundle (FOB); a lens such as a calcium fluoride lens (CaF2 fore optic) configured to focus light that is scattered from the ore sample onto the tip of the input fiber-optic bundle; and/or a cold-mirror configured at a 45° angle and between the broadband spectral light source and the ore sample, and also configured to transmit a near-infrared portion of a spectrum and reflect a visible portion of the spectrum. The cold mirror may be configured to reflect heat generated by the visible portion of the spectrum in order to keep the ore sample from becoming heated. The apparatus may also include a color CCD camera, e.g., arranged or configured on the opposite side of the cold mirror, that is configured to view the reflection of the ore sample and captures a digital image; and/or include a laser pattern generator configured in the path of the color CCD camera and also configured to project a reticle onto the surface of the ore sample. The FOB may be configured as a bifurcated FOB having two inputs for one output, including where one half of the bifurcated FOB is configured to feed the spectrometer, and the other half of the bifurcated FOB is configured to illuminate with a high power LED. The high power LED may be configured to back-light the bifurcated FOB and project a back-lit footprint of the area that is seen by the spectrometer. The back-lit footprint may be overlaid on the reticle projected and surface of the ore sample.

According to some embodiments of the present invention, the apparatus may include a rotary mechanism having a transparent holder configured to receive the ore sample placed therein. During a measurement, the rotary mechanism may be configured to rotate the ore sample, and the tip of the FOB or the calcium fluoride lens may be configured to translate radially. The measurement may include a number of sub-aperture regions of the ore sample. The signal processor or signal processing module may be configured to provide an average TBC of the ore sample and can provide a percent variability of TBC within the ore sample. The rotary mechanism may include a similar holder configured to hold a spectrolon reflectance reference target in the same plane as the measurement surface of the ore sample. The rotary mechanism and radial translation could be replaced by an X-Y scanning mechanism to accomplish the same measurement sampling coverage. A reference spectrum may be taken immediately prior to the measurement of each sample.

According to some embodiments of the present invention, all components of the apparatus may be subjected to a temperature/humidity test that encompasses non-operational environmental extremes that the apparatus can encounter. The apparatus may include temperature sensors placed on critical components to provide feedback when operational temperatures are achieved, including where the apparatus will not turn on until the operational temperatures are met.

According to some embodiments of the present invention, the apparatus may include a fiber optic bundle (FOB) configured to illuminate and view the ore sample in-situ, including where the FOB is configured as an umbilical connecting a measurement head to a main processing module having the signal processor or signal processing module.

Drive-Through Device, Structure or Apparatus

According to some embodiments of the present invention, the apparatus may take the form of, or form part of, a drive-through apparatus, structure or device having an array of sensor configured to receive a haul truck loaded with a payload of bitumen ore that can pass under the array of sensors, and also configured to analyze the top surface of the payload of the haul truck. The drive-through apparatus, structure or device may be configured to scan haul trucks as they drive through. The apparatus may also form part of a system having a plurality of the drive-through apparatus, structure or device, each for being deployed at an exit of each mine or pit or along a main road that sees all of the truck traffic in the mine or pit. The signal processor or signal processing module may be configured to determine a total payload volume of the payload of a haul truck, including based at least partly on knowledge of the model of the truck bed. The drive-through apparatus, structure or device may be configured to span the width of the road and have the array of sensors mounted high enough for the trucks to drive underneath. By way of example, the drive-through apparatus, structure or device may be configured as two half arches with a separate package of the array of sensors on each half; or as a bridge that spans an entire road and has several sensor array modules that can move to intercept the haul trucks as they drive beneath, including where the bridge is configured with catwalks for maintenance.

According to some embodiments of the present invention, the apparatus may comprise generators at each installation configured to provide power.

According to some embodiments of the present invention, the apparatus may comprise a wireless communication system for exchanging data and control signaling between the apparatus and a remote site, including one being managed by off-site personnel.

According to some embodiments of the present invention, the array of sensors may include light sources configured as broadband spectral lamps or discrete wavelength lasers or LEDs.

According to some embodiments of the present invention, the array of sensors may be configured to start a measurement at a correct height and change the height and angle during the measurement to follow the contour of the payload in the bed of the haul truck in order to maintain a sufficient signal-to-noise ratio to provide a reliable measurement. The array of sensors may be configured with projection optics to provide sufficient illumination in order to cover a larger measurement area; with large aperture collecting optics to capture enough scattered light for spectrometer/detectors to provide an answer to the percent weight of Total Bitumen Content; with an array of down looking range finders mounted to a support structure in order to analyze the volume of the payload in the bed of the haul truck; or to build a topographic map of the payload as the haul truck passes underneath.

Haul Truck Bed Implementations

According to some embodiments of the present invention, the apparatus may include, or form part of, a device, a piece of equipment or further apparatus configured to be placed in the bed of a haul truck. The instrumented truck bed is configured for analysis of each scoopful or shovelful of ore as it is added to the haul truck.

According to some embodiments of the present invention, the apparatus may include, or form part of, a system having a plurality of devices, pieces of equipment or further apparatuses, each configured to be placed in the bed of a haul truck at an appropriate respective height, including each being spaced at a respective height corresponding to a respective shovel load, for providing a better understanding of the entire load compared to a single top surface measurement. The apparatus may include, or form part of, a distributed acoustic array, including an acoustic source if need, configured to be placed in a bed of a haul truck. The apparatus may comprise ruggedized fiber optic sensors configured to be placing in each of the four corners of the truck bed, and configured to capture an entire volume of the payload in the haul truck, including where the acoustic source to provide an acoustic signal is configured as a solenoid the strikes the bottom of the truck bed when energized.

According to some embodiments of the present invention, the apparatus may include, or form part of, the bed of the haul truck or the haul truck itself.

BRIEF DESCRIPTION OF THE DRAWING

The drawing includes FIGS. 1-8, which are not necessarily drawn to scale, as follows:

FIG. 1 includes FIGS. 1a and 1b, where FIG. 1a is a block diagram showing the basic apparatus of the present invention, and FIG. 1b is a block diagram of a signal processor or signal processing module that forms part of the apparatus shown in FIG. 1a, all according to some embodiments of the present invention.

FIG. 2 includes FIGS. 2a, 2b and 2c, where FIG. 2a is a photograph of an ore pit; FIG. 2b is a local "worked" ore face visualization of a part of the ore pit in FIG. 2a using a camera; and FIG. 2c is a visualization system output of the local "worked" ore face visualization in FIG. 2b that provides a false color map of bitumen content in the ore face, all according to some embodiments of the present invention.

FIG. 3a shows a camera with a filter wheel; FIG. 3b shows a binocular differential waveband system; and FIG. 3c shows a cameral with integrated pixel filters, all according to some embodiments of the present invention.

FIG. 6 is an illustration of a drive-through apparatus, structure or device according to some embodiments of the present invention.

FIG. 7 is a picture of a haul truck with a payload of bitumen ore.

FIG. 8 is an illustration of a haul truck bed configured with apparatus according to some embodiments of the present invention.

DETAILED DESCRIPTION OF BEST MODE OF THE INVENTION

FIG. 1: The Basic Apparatus

FIG. 1 includes FIGS. 1a and 1b, where FIG. 1a shows apparatus 10 having a signal processor or signal processing module 12 configured to receive signaling containing information about images of an ore sample; and determine information about a Bitumen Content of the ore sample based at least partly on the signaling, including for use in real time ore blend management in a bitumen recovery process related to mined oil sands.

The apparatus 10 may be used to provide a real time ore face ore grade visualization e.g., for analyzing a part or section of an ore pit or mine, consistent with that set forth below in relation to FIGS. 2-3.

Figure 4:
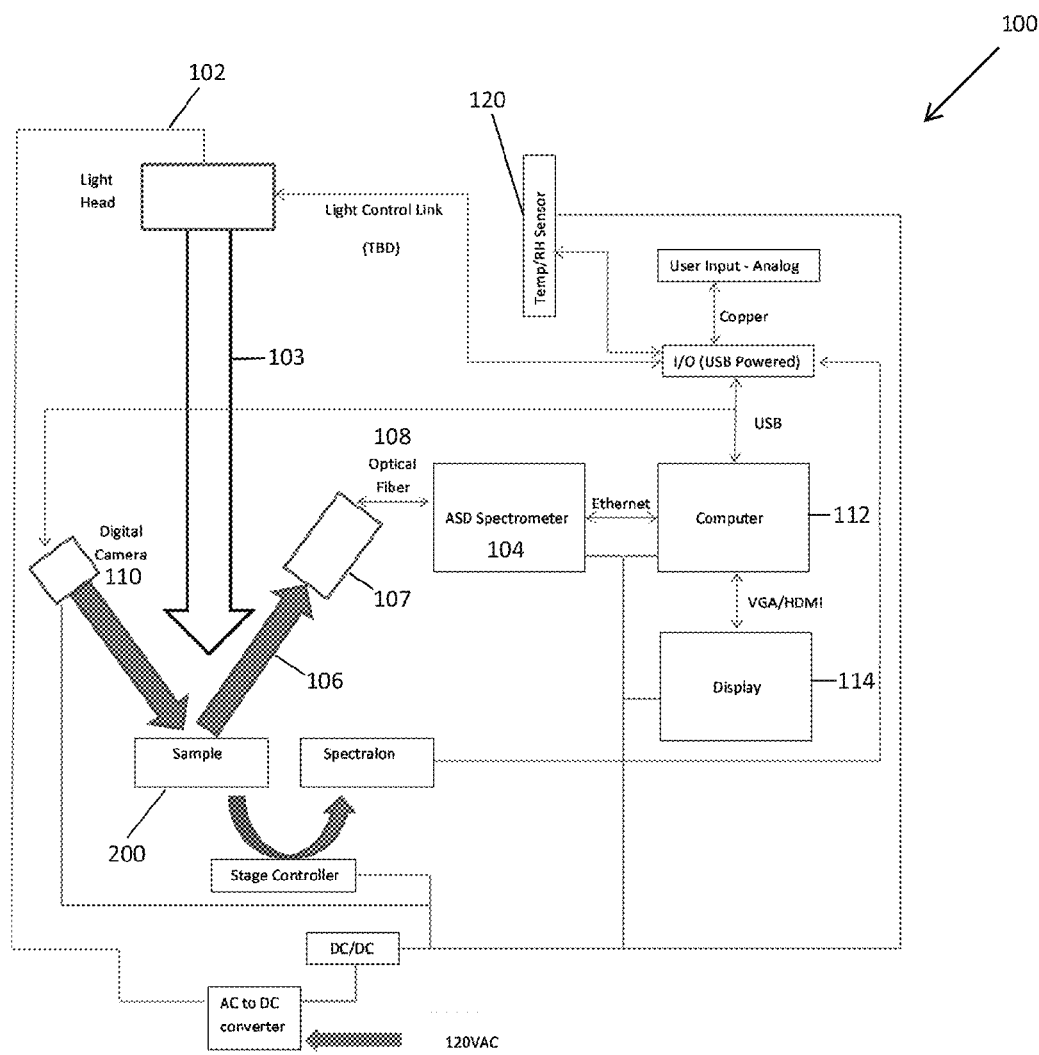
FIG. 4 is a system block diagram according to some embodiments of the present invention.
Figure 5A:
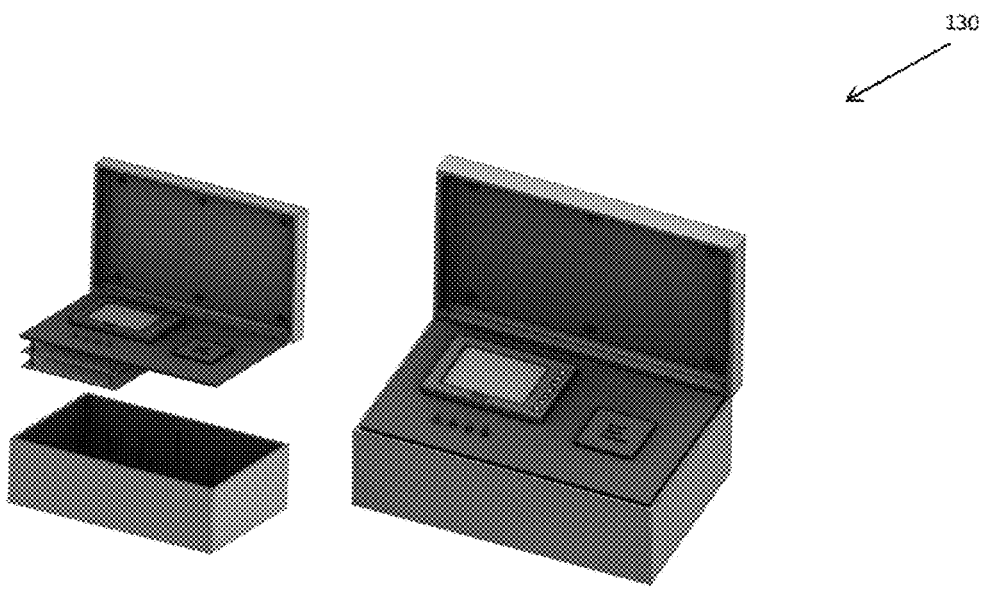
FIG. 5a is a geology tool according to some embodiments of the present invention.
Figure 5B:
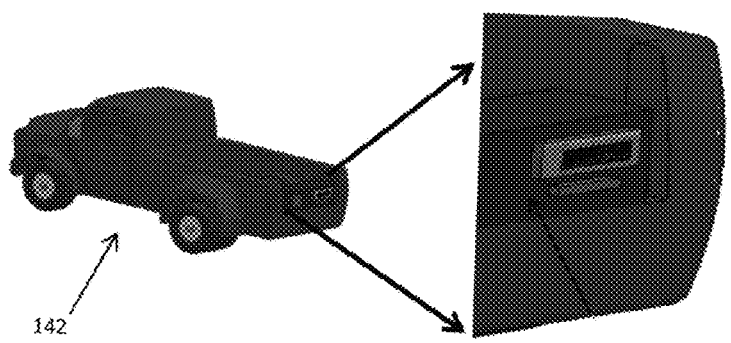
FIG. 5b is a geology tool according to some embodiments of the present invention.
Figure 5C:
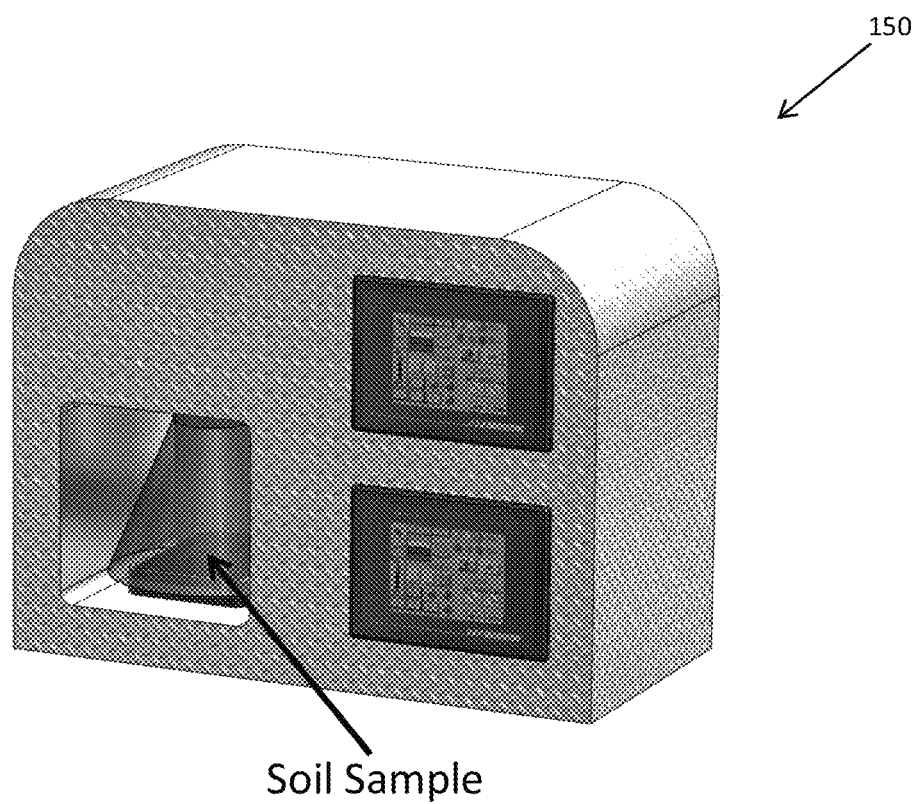
FIG. 5c is a geology tool according to some embodiments of the present invention.

The apparatus 10 may take the form of, or be used in relation to, a portable analyzer, instrument, or geology tool, e.g., to provide Total Bitumen Content (TBC) by percentage weight, e.g., for analyzing an ore sample from a payload of ore in the bed of a haul truck at an ore pit or mine, consistent with that set forth herein in relation to FIGS. 4-5c.

The apparatus 10 may form part of, or be used to provide or implement, a drive-through device, structure or apparatus, e.g., for analyzing a payload of ore in the bed of a haul truck at an ore pit or mine, consistent with that set forth herein in relation to FIG. 6.

The apparatus 10 may form part of, or be used to provide or implement, a haul truck bed configuration, e.g., for analyzing one or more shovel buckets of ore dumped in a payload in the bed of a haul truck at an ore pit or mine, consistent with that set forth herein in relation to FIGS. 7-8.

By way of example, FIG. 1*b* shows the signal processor or signal processing module 12 that forms part of the apparatus 10 in FIG. 1*a*. The signal processor or signal processing module 12 may be configured with a combination 14 of at least one processor and at least one memory including computer program code, where the at least one memory and the computer program code are configured, with the at least one processor, to cause the apparatus 10 at least to receive the signaling and determine the information about the Bitumen Content of the ore sample. The signal processor or signal processing module 12 may also be configured to provide corresponding signaling containing the information about the Bitumen Content of the ore sample, e.g., for subsequent processing, consistent with that set forth herein.

Figure 3:
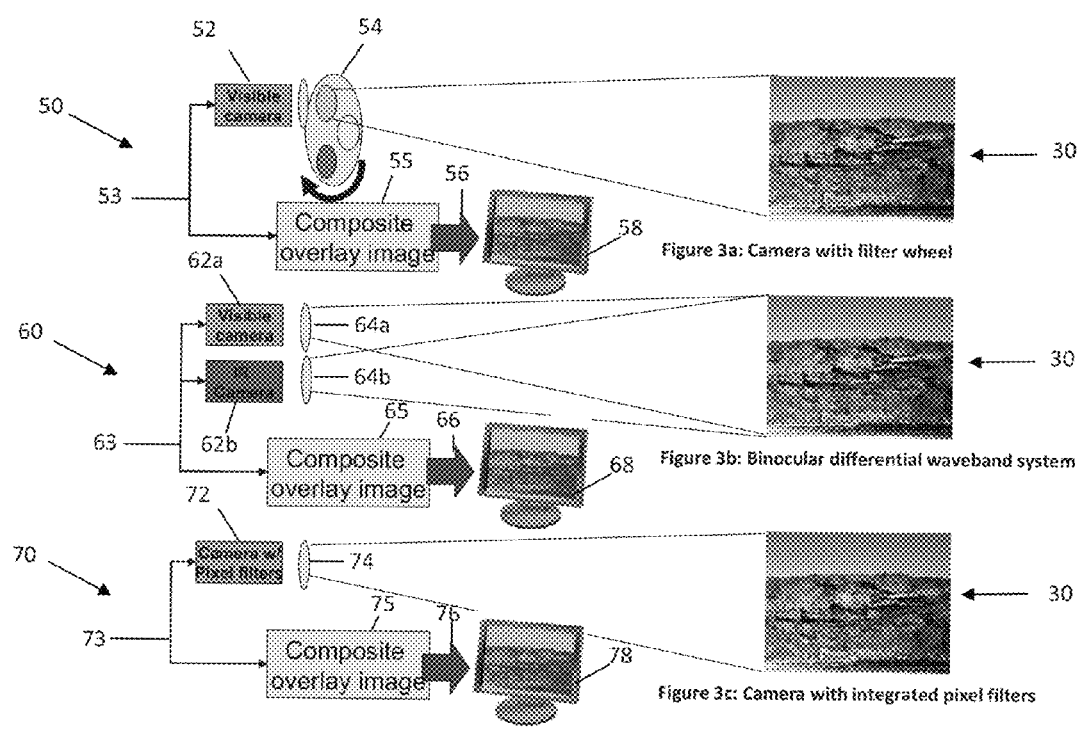
FIG. 3 includes FIGS. 3a, 3b and 3c and shows examples of approaches for spectral analysis of an ore face, where

FIGS. 2-3: Real Time Ore Face Ore Grade Visualization

According to some embodiments of the present invention, the present invention may be configured to provide a real time ore face ore grade visualization.

For example, the present invention may be implemented in the form of a technique in which a mine-face shovel operator is provided with a way to assess, in real time, the grade quality of the ore being excavated, providing either confirmation that the ore is of the expected grade, or allowing selective recovery/excavation to ensure the appropriate grade is mined at that location, consistent with that shown in FIGS. 2-3.

FIG. 2*a* shows an ore pit or mine generally indicated 20. FIG. 2*b* shows a local "worked" ore face visualization generally indicated as 30 of a part or section 22 of the ore pit or mine 20 in FIG. 2*a* using a camera system 32 having a single or multiple cameras capable of differential spectral image capture in visible and infrared (IR) regions. FIG. 2*c* shows a visualization system output generally indicated as 40 of the local "worked" ore face visualization 30 in FIG. 2*b* that provides a false color map of Bitumen Content in part or section 22 of the ore face or mine 22 (FIG. 2*a*). The scale on the right side of the visualization system output 40 shows greyscale coloration of the Bitumen Content ranging from >8%, >10%, >12%.

In operation, the part or section 22 of the ore face in the ore pit 20 in FIG. 2*a* is imaged using the camera system 32 having the single or multiple cameras as shown in FIG. 2*b* and images are taken at various wavelength ranges and particular discrete wavelengths. Of particular interest are wavelength at which bitumen strongly absorbs light (visible, UV or IR), and a composite picture of the ore face is built. This composite picture identifies the regions of bitumen-rich ore through a false color encoding of the image shown in FIG. 2*c*, i.e., where strong absorption in reflected light (daylight or other illumination) is induced by the bitumen in the surface layers, the ore grade is indicated as most rich, etc.

Since hauling trucks (e.g., see FIGS. 6-8) that transport the ore from the ore pit or mine 20 to a process plant (not shown) may be all centrally dispatched to and from operating shovels in the pit or mine at a given time, and may be GPS controlled, etc., the system according to the present invention may also allow a mine operations team to assess real-time the grade quality of any given truck load, and schedule payloads into the process plant in order to minimize the blended ore grade variability.

FIG. 3 shows examples of optical arrangements to implement the present invention, which may take various forms, including those shown in FIGS. 3*a*, 3*b*, 3*c*.

For example, FIG. 3*a* shows an optical arrangement generally indicated as 50 having a single camera 52 with a filter wheel 54, where the camera 52 takes images of the local "worked" ore face visualization 30, e.g., of the part or section 22 of the ore pit or mine 20 in FIG. 2*a*, through the filter wheel 54, and provides signaling to a signal processor 55 configured to determine a composite overlay image and provide a composite overlay image signal indicated as 56 that may be displayed on a monitor 58 for viewing by the mine-face shovel operator or the mine operations team. The image on the monitor 58 as shown corresponds to the image 40 shown in FIG. 2*c*, and contains the information about the Bitumen Content of the local "worked" ore face visualization 30, e.g., of the part or section 22 of the ore pit or mine 20 in FIG. 2*a*.

FIG. 3*b* shows an optical arrangement that takes the form of a binocular differential wavelength system generally indicated as 60 having a pair of cameras 62*a*, 62*b* tuned to different wavelength ranges and corresponding lens 64*a*, 64*b*, where the cameras 62*a*, 62*b* take the images of the local "worked" ore face visualization 30, e.g., of the part or section 22 of the ore pit or mine 20 in FIG. 2*a*, through the corresponding lens 64*a*, 64*b*, and provide signaling 63 to a signal processor 65 configured to determine a composite overlay image and provide a composite overlay image signal indicated as 66 that may be displayed on a monitor 68. The image on the monitor 68 as shown corresponds to the image 40 shown in FIG. 2*c*, and contains the information about the Bitumen Content of the local "worked" ore face visualization 30, e.g., of the part or section 22 of the ore pit or mine 20 in FIG. 2*a*.

FIG. 3*c* shows an optical arrangement generally indicated as 70 that takes the form of a camera with integrated pixel filters 72 having an integrated single detector array with pixels tuned to particular wavelengths of interest and a corresponding lens 74. The camera 72 take the images of the local "worked" ore face visualization 30, e.g., of the part or section 22 of the ore pit or mine 20 in FIG. 2*a*, through the lens 74 and provide signaling 73 to a signal processor 75 configured to determine a composite overlay image and provide a composite overlay image signal indicated as 76 that may be displayed on a monitor 78. The image on the monitor 78 as shown corresponds to the image 40 shown in FIG. 2*c*, and contains the information about the Bitumen Content of the local "worked" ore face visualization 30, e.g., of the part or section 22 of the ore pit 20 in FIG. 2*a*.

In each optical arrangement in FIGS. 3*a*, 3*b*, 3*c*, the corresponding processors 55, 65, 75 may be implemented, e.g., using the apparatus 10 shown in FIG. 1, consistent with that set forth herein, including where the signal processor or signal processing module 12 is adapted to, or forms part of, a mining shovel in the form of an instrumented shovel. In each case, the measurement of interest would rely on developing a contrast model/image from two images: One which is not dependent on the bitumen content (e.g., most likely to be the visible range or portion of), and one in which the bitumen absorbs strongly—e.g., near, short or mid infrared wavelengths. These images are then contrast to each other (ratioed) to produce the image highlighting the bitumen.

FIG. 3 illustrates various possible optical arrangements or configurations, by way of example, and is not intended to be an exhaustive set of examples—simply examples of the optical configurations that may be used. As a person skilled in the art would appreciate, visible and IR cameras like elements 52, 62a, 62b, filter wheels like element 54, lens like elements 64a, 64b, 74 and monitors like elements 58, 68 and 78 are all known in the art, and the scope of the invention is not intended to be limited to any particular type or kind thereof either now known or later developed in the future.

FIGS. 4-5c: Total Bitumen Content by Percentage Weight

The present invention provides an instrument, e.g., that may be mounted directly onto, or in relation to, an operating shovel in the ore pit or mine, consistent with that set forth herein. According to some embodiments of the present invention, the instrument may take the form of a portable analyzer that is configured to provide the Total Bitumen Content (TBC), e.g., of an ore sample. The portable analyzer may also be known or referred to herein as a geology tool, that will determine the TBC by percent weight through a spectroscopic technique that ratios several different absorption wavelengths of clay, water and bitumen.

FIG. 4 shows a generalized block diagram generally indicated as 100 of one possible configuration for implementation such an instrument, portable analyzer, or geology tool, according to some embodiments of the present invention.

For example, the system 100 may include a light head such as element 102 that may be configured as a broadband spectral light source and used to illuminate an ore sample such as element 200 with broadband spectral light 103. A spectrometer such as element 104 may be configured to measure scattered light 106 from the ore sample 200 via an input fiber optic bundle (FOB), such as element 108. For testing purposes, a lens, such as a calcium fluoride lens (CaF2 fore optic), not shown, may also be configured to focus light that is scattered from the ore sample 200 onto the tip of the fiber-optic bundle 108.

According to some embodiments of the present invention, at a 45° angle and between the broadband source 102 and the ore sample 200, a cold-mirror such as element 107 may be configured that transmits the near-infrared portion of the spectrum and reflects the visible portion of the spectrum. The cold mirror 107 may be configured to reflect heat generated by the visible portion of the spectrum. This helps keep the ore sample from becoming heated. For example, on the opposite side of the cold mirror 107, a color CCD camera such as 110 may be configured to view the reflection of the ore sample 200 and capture a digital image.

The system 100 may be configured with a computer or signal processor such as element 112 and a display such as element 114, where the computer or signal processor 112 may be configured to implement the functionality consistent with the apparatus 10 shown in FIG. 1, and where the display 114 may be configured to implement the functionality consistent with the monitors 58, 68 and 78 shown in FIGS. 3a, 3b, 3c respectively.

According to some embodiments of the present invention, a laser pattern generator, not shown, may also be configured in the path of the CCD camera 110 that projects a reticle onto the surface of the ore sample 200. The reticle provides a scale that can be helpful or used for measuring or aiming.

According to some embodiments of the present invention, the FOB may be configured as a device that has two inputs for one output. This configuration is known as a bifurcated FOB, where one half of the bifurcated FOB is configured to feed the spectrometer 104, and where the other half is configured to be illuminated with a high power LED. The high power LED is configured to back-light the FOB and projects the footprint of the area that is seen by the spectrometer 104.

According to some embodiments of the present invention, the back-lit footprint may be overlaid on the projected reticle and surface of the ore sample 200. For each measurement, a detailed digital image is captured.

According to some embodiments of the present invention, the ore sample, such as element 200, may be placed into a transparent holder that is held in a rotary mechanism (not shown). During the measurement, the ore sample 200 may be rotated and the lens, e.g., the CaF2 fore optic, may be translated radially. A measurement may include a number of sub-aperture regions of the ore sample. This method provides the average Total Bitumen Content (TBC) of the ore sample and can provide a percent variability of TBC within the ore sample.

According to some embodiments of the present invention, in a similar holder, a Spectrolon reflectance reference target may be held in the same plane as the measurement surface of the ore sample. A reference spectrum may be taken immediately prior to the measurement of each sample.

All components of the system 100 may be subjected to a temperature/humidity test that encompasses the non-operational environmental extremes that the device can encounter. Temperature sensors, like elements 120, may be placed on critical components to provide feedback when operational temperatures are achieved. The geology tool will typically not be turned on, e.g., until the operational temperatures are met.

According to some embodiments of the present invention, other configurations of the geology tool can implement discrete test wavelengths from tunable lasers, multiple lasers or LEDs for illuminating the ore sample. Another configuration could use the FOB to illuminate and view the ore in-situ. This configuration would see the FOB as an umbilical connecting the measurement head to the main processing module.

FIGS. 5a, 5b, 5c show different embodiments of the instrument, portable analyzer, or geology tool 130, 140, 150, respectively. The instruments, portable analyzers, or geology tools 130, 150 are shown as free standing devices, while the instrument, portable analyzer, or geology tool 140 is shown arranged or configured on or in the back of a truck 142.

FIG. 6: Drive-Through Device, Structure or Apparatus

According to some embodiments, the present invention make take the form of, or form part of, a drive-through device, structure, apparatus or platform generally indicated as 300 having an array of sensors 302a, 302b configured or arranged on an arch or bridge-like structure 304.

As shown, a heavy haul truck generally indicated as 310 loaded with bitumen ore 312 will pass under the array of sensors 302a, 302b that will analyze the top surface of the payload of bitumen ore 312. This drive-through device, structure, apparatus or platform 300 can be deployed at the exit of each pit or along a main road that sees all of the truck traffic. The primary intent of the drive-through device, structure, apparatus or platform 300 is to provide a percent weight of the Total Bitumen Content (TBC) of the truck payload, although it is possible that other analyses can be performed such as total payload volume, etc.

The drive-through device, structure, apparatus or platform 300 may be configured to span the width of the road and has the sensor array 302a, 302b mounted high enough for the trucks like truck 310 to drive under. The drive-through device, structure, apparatus or platform 300 has been envisioned as two half arches 306a, 306b that combine to form the arch or bridge-like structure 304 with a separate sensor array package 302a, 302b on each half. In FIG. 4, the two half arches 306a, 306b are shown supported by supports 308a, 308b having strut-like portions 309a, 309b coupling the two half arches 306a, 306b to the supports 308a, 308b. The supports 308a, 308b are mounted on mounting plates 320a, 320b. Another version could be a "Bridge" that spans the entire road and has several sensor array modules that can move to intercept the trucks as they drive beneath. The bridge could also have catwalks (not shown) for maintenance.

In either case, the drive-through device, structure, apparatus or platform 300 may have its own power supplied by generators (not shown) at each installation. Data and control will be wireless and may be managed off site by proprietary personnel.

The drive-through device, structure, apparatus or platform 300 will extend the stand-off distance and measurement area of the configurations shown in relation to FIGS. 4-5c. Consistent with that set forth above, the drive-through device, structure, apparatus or platform 300 may include light sources that may be broadband spectral lamps or discrete wavelength lasers or LEDs. One of the technical challenges related to the implementation of the drive-through device, structure, apparatus or platform 300 is to maintain a sufficient signal-to-noise (S/N) ratio to provide a reliable measurement. In order to accomplish the desired S/N ration, the sensor payload may be articulated to start the measurement at the correct height and change height and angle during the measurement to follow the contour of the payload in the bed of the truck.

Another change form the configurations shown in relation to FIGS. 4-5c and the drive-through device, structure, apparatus or platform 300 shown in FIG. 6 is that the light source will need to cover a much larger measurement area. This will require the projection optics to be configured to provide sufficient illumination. Large aperture collecting optics may also be used to capture enough scattered light for the spectrometer/detectors to provide an answer to the percent weight of TBC.

To analyze the volume of the payload in the bed of the truck, an array of down looking range finders may be mounted to the support structure. As the truck passes under the bridge a topographic map of the payload can be built and with knowledge of the model of the truck bed, a signal processor like element 10 in FIG. 1a may be configured to calculate the volume.

FIGS. 7-8: Haul Truck Bed Implementations

When using the drive-through device, structure, apparatus or platform 300 set forth about in relation to FIG. 6, a heavy haul truck loaded 400 with a payload 402 of bitumen ore as shown in FIG. 7 will pass under the array of sensors 302a, 302b that will analyze the top surface of the payload. One disadvantage of this type of measurement is that the array of sensors 302a, 302b can only see ore from the last shovel load put on the truck. It is possible that the ore from beneath the surface is very different from the top surface.

According to some embodiments of the present invention, information may be provided in relation to each shovel load in the truck bed.

FIG. 8 illustrates one possible way to implement the present invention in the bed of such a heavy haul truck like 500, according to some embodiments of the present invention. For example, the heavy haul truck 500 may be configured to include four instruments, analyzers, or geology tools according to the present invention like elements 502a, 502b, 502c, 502d, which are each respectively placed at different levels in the bed 504 of the truck 500 for analyzing shovel buckets, e.g., #1, #2, #3, #4, dumped sequentially into the bed 504, according to some embodiments of the present invention. Each instruments, analyzers, or geology tools 502a, 502b, 502c, 502d may include the apparatus 10 shown in FIG. 1 for analyzing shovel buckets based at least partly on determining information about the Bitumen Content of the ore sample in each shovel bucket, e.g., for use in real time ore blend management in a bitumen recovery process related to mined oil sands, consistent with that set forth herein.

By exploiting the instruments, analyzers, or geology tools, e.g., as set forth in relation to FIGS. 1, 4 and 5a-5c, the complexity and risk of increased stand-off distance in relation to the embodiment set forth in relation to FIG. 6 may be eliminated. In addition, accuracy of the Total Bitumen Content (TBC) of the load in the truck 500 may be increased with the number of samples measured. With the instruments, analyzers, or geology tools, e.g., as set forth in relation to FIGS. 1, 4 and 5a-5c, placed at the appropriate height in the truck bed 504, i.e. one for each shovel load, e.g., shovel load #1, #2, #3, #4, provides a better understanding of the entire load compared to the single top surface measurement of the drive-through device, structure, apparatus or platform 300 set forth in relation to FIG. 6

The number of instruments, analyzers, or geology tools, e.g., as set forth in relation to FIGS. 1, 4 and 5a-5c, can be increased for providing even better knowledge of the ore in the truck.

According to some embodiments of the present invention, another configuration of an instrumented truck bed may be to install a distributed acoustic array and, if necessary, an acoustic source. By placing ruggedized fiber optic sensors in each of the four corners of the truck bed, it may be possible to capture the entire volume of the payload in the truck. The source for the acoustic signal could be a simple solenoid the strikes the bottom of the truck bed when energized.

Signal Processor or Signal Processing Module 12

By way of example, and consistent with that described herein, the functionality of the signal processor or signal processing module 12 may include a signal processing device or signal processor that may be implemented to receive a signal, or provide a signal, or process signals therein, using hardware, software, firmware, or a combination thereof, although the scope of the invention is not intended to be limited to any particular embodiment thereof. In a typical software implementation, the signal processor would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality set forth herein, as well as other functionality described herein without undue experimentation. The scope of the invention is not intended to be limited to any particular implementation using technology now known or later developed in the future. Moreover, the scope of the invention is intended to include a signal processor as either part of the aforementioned devices, as a stand alone module, or in the combination with other circuitry for implementing another module.

It is also understood that the apparatus 10 may include one or more other modules, components, processing circuits, or circuitry for implementing other functionality associated with the underlying apparatus that does not form part of the underlying invention, and thus is not described in detail herein. By way of example, the one or more other modules, components, processing circuits, or circuitry may include random access memory, read only memory, input/output circuitry and data and address buses for use in relation to implementing the signal processing functionality of the signal processor, or devices or components, etc.

Applications

The present invention may also be used in, or form part of, or used in conjunction with, industrial processes like a mineral extraction processing system for extracting minerals from ore either now known or later developed in the future, including any mineral process, such as those related to processing substances or compounds that result from inorganic processes of nature and/or that are mined from the ground, as well as including either other extraction processing systems or other industrial processes, where the sorting, or classification, of product by size is critical to overall industrial process performance.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus comprising:
    a signal processor or signal processing module configured to
    receive signaling containing information about images of an ore sample; and
    determine corresponding signaling containing information about a Bitumen Content of the ore sample based at least partly on the signaling, including for use in real time ore blend management in a bitumen recovery process related to mined oil sands;
    wherein the ore sample is an ore face, and the signaling contains information about the images of the ore face; and
    wherein the signal processor or signal processing module is configured to determine a real time ore face ore grade visualization based at least partly on the signaling.

2. Apparatus according to claim 1,
    wherein the signal processor or signal processing module is adapted to, or forms part of, a mining shovel in the form of an instrumented shovel.

3. Apparatus according to claim 1, wherein the signal processor or signal processing module is configured to provide the corresponding signaling containing information about the real time ore face ore grade visualization, including a composite overlay image.

4. Apparatus according to claim 2, wherein the signaling is received from a single or multiple cameras that image the ore face, including being adapted to, or forming part of, the mining shovel in of the instrumented shovel.

5. Apparatus according to claim 4, wherein the images are taken at various wavelength ranges and particular discrete wavelengths.

6. Apparatus according to claim 5, wherein the particular discrete wavelengths include a wavelength at which bitumen strongly absorbs light, including visible, ultraviolet (UV) or infrared (IR), and a composite picture of the ore face is built.

7. Apparatus according to claim 6, wherein the composite picture identifies regions of bitumen-rich ore through a false color encoding of the image, including where strong absorption in reflected light, such as daylight or other illumination, is induced by the bitumen in surface layers, and the ore grade is indicated as most rich.

8. Apparatus according to claim 1, wherein the real time ore face ore grade visualization provides for the ability, including by a mine-face operating shovel operator, to assess in real time, the grade quality of the ore being excavated, either providing confirmation that the ore is of an expected grade, or allowing a selective recovery/excavation to ensure an appropriate grade is mined at that location.

9. Apparatus according to claim 1, wherein the apparatus forms part of a GPS controlled system having hauling trucks that transport the ore to a process plant, each hauling truck configured with a respective signal processor, and the hauling trucks centrally dispatched to and from operating shovels in a mine at a given time, where the GPS system allows for the ability, including by a mine operations team, to assess real-time the grade quality of any given truck load, and schedule payloads into the process plant in order to minimize substantially a blended ore grade variability.

10. Apparatus according to claim 1, wherein the apparatus comprises an optical arrangement configured to receive the images of the ore face and provide a composite overlay image containing information about the images of the ore face.

11. Apparatus according to claim 10, wherein the optical arrangement comprises:
    a single camera with a filter wheel;
    a pair of camera tuned to different wavelength ranges, including a binocular differential waveband system having a visible camera and an infrared (IR) camera; or
    an integrated single detector array with pixels tuned to particular wavelengths of interest, including a camera with pixel filters.

12. Apparatus according to claim 10, wherein, in each optical arrangement, a measurement of interest relies on developing a contrast model/image from two images: one which is not dependent on the bitumen content, including the visible range or portion, and one in which the bitumen absorbs strongly, including near, short or mid infrared wavelengths.

13. Apparatus according to claim 10, wherein one image which is not dependent on the bitumen content is in a visible range or portion, and the other image in which the bitumen absorbs strongly is near, short or mid infrared wavelengths.

14. Apparatus according to claim 12, wherein the signal processor or signal processing module is configured to contrast the two images to each other, including being ratioed to produce a corresponding image highlighting the bitumen.

15. Apparatus according to claim 1, wherein the signal processor or signal processing module comprises:
a combination of at least one processor and at least one memory including computer program code, where the at least one memory and the computer program code are configured, with the at least one processor, to cause the apparatus at least to receive the signaling and determine the real time ore face ore grade visualization.

16. Apparatus according to claim 3, wherein the apparatus comprises the single or multiple cameras.

17. Apparatus according to claim 1, wherein the apparatus comprises, or forms part of, a device, a piece of equipment or further apparatus configured to be placed in the bed of a haul truck.

18. Apparatus according to claim 1, wherein the apparatus comprises, or forms part of, a distributed acoustic array, including an acoustic source if need, configured to be placed in a bed of a haul truck.

19. Apparatus comprising:
a signal processor or signal processing module configured to
receive signaling containing information about images of an ore sample; and
determine information about a Bitumen Content of the ore sample based at least partly on the signaling, including for use in real time ore blend management in a bitumen recovery process related to mined oil sands;
wherein the signal processor or signal processing module is configured to determine a Total Bitumen Content (TBC) by percent weight through a spectroscopic technique that ratios several different absorption wavelengths of clay, water and bitumen in the ore sample.

20. Apparatus according to claim 19, wherein the signal processor or signal processing module forms part of a portable analyzer, instrument or geology tool.

21. Apparatus according to claim 19, wherein the apparatus comprises a broadband spectral light source configured to illuminate the ore sample.

22. Apparatus according to claim 21, wherein the apparatus comprises a spectrometer configured to measure scattered light from the ore sample, including via an input fiber optic bundle (FOB).

23. Apparatus according to claim 22, wherein the apparatus comprises a lens, including a calcium fluoride lens, configured to focus light that is scattered from the ore sample onto the tip of the input fiber-optic bundle.

24. Apparatus according to claim 23, wherein the apparatus comprises a cold-mirror configured at a 45° angle and between the broadband spectral light source and the ore sample, and also configured to transmit a near-infrared portion of a spectrum and reflect a visible portion of the spectrum.

25. Apparatus according to claim 24, wherein the cold mirror is configured to reflect heat generated by the visible portion of the spectrum in order to keep the ore sample from becoming heated.

26. Apparatus according to claim 25, wherein the apparatus comprises a color CCD camera configured to view the reflection of the ore sample and captures a digital image.

27. Apparatus according to claim 26, wherein the apparatus comprises a laser pattern generator configured In the path of the color CCD camera and also configured to project a reticle onto the surface of the ore sample.

28. Apparatus according to claim 22, wherein the FOB is configured as a bifurcated FOB having two inputs for one output.

29. Apparatus according to claim 28, wherein one half of the bifurcated FOB is configured to feed the spectrometer, and the other half of the bifurcated FOB is configured to illuminate with a high power LED.

30. Apparatus according to claim 29, wherein the high power LED is configured to back-light the bifurcated FOB and project a back-lit footprint of the area that is seen by the spectrometer.

31. Apparatus according to claim 30, wherein the back-lit footprint is overlaid on the reticle projected and surface of the ore sample.

32. Apparatus according to claim 30, wherein the apparatus comprises a rotary mechanism having a transparent holder configured to receive the ore sample placed therein.

33. Apparatus according to claim 32, wherein, during a measurement, the rotary mechanism is configured to rotate the ore sample, and a lens is configured to translate radially.

34. Apparatus according to claim 32, wherein the measurement is comprised of a number of sub-aperture regions of the ore sample.

35. Apparatus according to claim 34, wherein the signal processor or signal processing module is configured to provide an average total Bitumen Content (TBC) of the ore sample and can provide a percent variability of TBC within the ore sample.

36. Apparatus according to claim 35, wherein the rotary mechanism comprises a similar holder configured to hold a spectrolon reflectance reference target in the same plane as the measurement surface of the ore sample.

37. Apparatus according to claim 36, wherein a reference spectrum is taken immediately prior to the measurement of each ore sample.

38. Apparatus according to claim 37, wherein all components of the apparatus are subjected to a temperature/humidity test that encompasses non-operational environmental extremes that the apparatus can encounter.

39. Apparatus according to claim 38, wherein the apparatus comprises temperature sensors placed on critical components to provide feedback when operational temperatures are achieved, including where the apparatus will not turn on until operational temperatures are met.

40. Apparatus according to claim 19, wherein the apparatus comprises tunable lasers, multiple lasers or LEDs configured to implement discrete test wavelengths for illuminating the ore sample.

41. Apparatus according to claim 19, wherein the apparatus comprises a fiber optic bundle (FOB) configured to illuminate and view the ore sample in-situ, including where the FOB is configured as an umbilical connecting a measurement head to a main processing module having the signal processor or signal processing module.

42. Apparatus comprising:
a signal processor or signal processing module configured to
receive signaling containing information about images of an ore sample; and
determine information about a Bitumen Content of the ore sample based at least partly on the signaling, including for use in real time ore blend management in a bitumen recovery process related to mined oil sands;
wherein the apparatus comprises a drive-through apparatus, structure or device having an array of sensor configured to receive a haul truck loaded with a payload of bitumen ore that can pass under the array of sensors, and also configured to analyze the top surface of the payload of the haul truck.

43. Apparatus according to claim 42, wherein the apparatus forms part of a system having a plurality of the drive-through apparatus, structure or device, each for being deployed at an exit of each pit or along a main road that sees all truck traffic in the ore pit.

44. Apparatus according to claim 42, wherein the signal processor or signal processing module is configured to determine a total payload volume of the payload of a haul truck, including based at least partly on knowledge of the model of the truck bed.

45. Apparatus according to claim 42, wherein the drive-through apparatus, structure or device is configured to span the width of a roadway and has the array of sensors mounted high enough for the trucks to drive underneath.

46. Apparatus according to claim 42, wherein the drive-through apparatus, structure or device is configured as two half arches with a separate package of the array of sensors on each half arch.

47. Apparatus according to claim 42, wherein the drive-through apparatus, structure or device is configured as a bridge that spans an entire roadway and has several sensor array modules that can move to intercept the haul trucks as they drive beneath.

48. Apparatus according to claim 42, wherein the apparatus comprises generators at each installation configured to provide power.

49. Apparatus according to claim 42, wherein the apparatus comprises a wireless communication system for exchanging data and control signaling between the apparatus and a remote site, including one being managed by off-site personnel.

50. Apparatus according to claim 42, wherein the array of sensors comprises light sources configured as broadband spectral lamps or discrete wavelength lasers or LEDs.

51. Apparatus according to claim 42, wherein the array of sensors is configured to start a measurement at a correct height and change height and angle during the measurement to follow the contour of the payload in the bed of the haul truck in order to maintain a sufficient signal-to-noise ratio to provide a reliable measurement.

52. Apparatus according to claim 42, wherein the array of sensors is configured with projection optics to provide sufficient illumination in order to cover a larger measurement area.

53. Apparatus according to claim 42, wherein the array of sensors is configured with large aperture collecting optics to capture enough scattered light for spectrometer/detectors to provide an answer to the percent weight of Total Bitumen Content.

54. Apparatus according to claim 42, wherein the array of sensors is configured with an array of down looking range finders mounted to a support structure in order to analyze the volume of the payload in the bed of the haul truck.

55. Apparatus according to claim 42, wherein the array of sensors is configured to build a topographic map of the payload as the haul truck passes underneath.

56. Apparatus comprising:
a signal processor or signal processing module configured to
receive signaling containing information about images of an ore sample; and
determine information about a Bitumen Content of the ore sample based at least partly on the signaling, including for use in real time ore blend management in a bitumen recovery process related to mined oil sands;
wherein the apparatus comprises, or forms part of, a system having a plurality of devices, pieces of equipment or further apparatuses, each configured to be placed in the bed of a haul truck at an appropriate respective height, including each being spaced at a respective height corresponding to a respective shovel load, for providing obtaining information about the entire load compared to a single top surface measurement.

57. Apparatus according to claim 56, wherein the apparatus comprises the bed of the haul truck or the haul truck itself.

58. Apparatus comprising:
a signal processor or signal processing module configured to
receive signaling containing information about images of an ore sample; and
determine information about a Bitumen Content of the ore sample based at least partly on the signaling, including for use in real time ore blend management in a bitumen recovery process related to mined oil sands;
wherein the apparatus comprises ruggedized fiber optic sensors configured to be placing in each of the four corners of the truck bed, and configured to capture an entire volume of the payload in the haul truck.

59. Apparatus according to claim 58, wherein the acoustic source to provide an acoustic signal is configured as a solenoid the strikes the bottom of the truck bed when energized.

* * * * *